(12) United States Patent  (10) Patent No.: US 9,376,968 B2
Surnilla et al.  (45) Date of Patent: *Jun. 28, 2016

(54) METHODS AND SYSTEMS FOR FUEL ETHANOL CONTENT DETERMINATION VIA AN OXYGEN SENSOR

(71) Applicant: Ford Global Technologies, LLC, Dearborn, MI (US)

(72) Inventors: Gopichandra Surnilla, West Bloomfield, MI (US); Daniel A. Makled, Dearborn, MI (US); Richard E. Soltis, Saline, MI (US); Jacobus Hendrik Visser, Farmington Hills, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 90 days.

This patent is subject to a terminal disclaimer.

(21) Appl. No.: 14/297,301

(22) Filed: Jun. 5, 2014

(65) Prior Publication Data

US 2015/0192085 A1  Jul. 9, 2015

Related U.S. Application Data

(63) Continuation-in-part of application No. 14/151,574, filed on Jan. 9, 2014.

(51) Int. Cl.
*F02D 19/08* (2006.01)
*F02D 19/06* (2006.01)
(Continued)

(52) U.S. Cl.
CPC .......... *F02D 19/087* (2013.01); *F02D 19/0634* (2013.01); *F02D 41/0025* (2013.01); *F02D 41/123* (2013.01); *F02D 41/1454* (2013.01);
(Continued)

(58) Field of Classification Search
CPC .............. F02D 19/0634; F02D 19/087; F02D 41/2445; F02D 41/2451; F02D 41/2454
USPC .................. 123/674, 688, 703, 575; 701/109; 60/276
See application file for complete search history.

(56) References Cited

U.S. PATENT DOCUMENTS 4,831,838 A * 5/1989 Nagai ................. F02D 41/2454
                                                   123/691
4,993,391 A * 2/1991 Kuribara ............. F02D 19/0605
                                                   123/1 A
(Continued)

FOREIGN PATENT DOCUMENTS

JP     2009150264 A  *  7/2009

OTHER PUBLICATIONS

Surnilla, Gopichandra et al., "Methods and Systems for Humidity Detection Via an Exhaust Gas Sensor," U.S. Appl. No. 13/745,639, filed Jan. 18, 013, 32 pages.
(Continued)

*Primary Examiner* — Mahmoud Gimie
(74) *Attorney, Agent, or Firm* — Julia Voutyras; Alleman Hall McCoy Russell & Tuttle LLP

(57) ABSTRACT

Methods are provided for accurately learning part-to-part variability of an intake or exhaust oxygen sensor. A correction factor is learned based on sensor readings at voltages above and below a voltage corresponding to dry air conditions. An ethanol transfer function is then adjusted based on the learned correction factor so as to improve the accuracy of combusted fuel ethanol content estimation.

20 Claims, 6 Drawing Sheets

(51) Int. Cl.
*G01M 15/10* (2006.01)
*F02D 41/12* (2006.01)
*F02D 41/24* (2006.01)
*F02D 41/00* (2006.01)
*F02D 41/14* (2006.01)

(52) U.S. Cl.
CPC ........ *F02D 41/2438* (2013.01); *F02D 41/2474* (2013.01); *G01M 15/104* (2013.01); *F02D 41/144* (2013.01); *F02D 41/1439* (2013.01); *F02D 41/1456* (2013.01); *F02D 41/2441* (2013.01); *F02D 2200/0418* (2013.01); *F02D 2200/0612* (2013.01)

(56) References Cited

U.S. PATENT DOCUMENTS

| | | | | |
|---|---|---|---|---|
| 5,090,389 | A | * | 2/1992 | Oota ............... F02D 41/0025 123/1 A |
| 5,145,566 | A | | 9/1992 | Logothetis et al. |
| 5,488,311 | A | * | 1/1996 | Kamioka ........... G01N 33/2852 324/674 |
| 6,227,033 | B1 | * | 5/2001 | Kainz ................ F02D 41/123 123/674 |
| 6,874,490 | B2 | * | 4/2005 | Surnilla ............. F02D 41/0032 123/198 DB |
| 8,296,042 | B2 | | 10/2012 | Xiao et al. |
| 8,495,996 | B2 | | 7/2013 | Soltis et al. |
| 8,522,760 | B2 | | 9/2013 | Soltis |
| 8,763,594 | B2 | | 7/2014 | Surnilla et al. |
| 2006/0289314 | A1 | * | 12/2006 | Schnaibel ........... G01N 27/419 205/782 |
| 2009/0093945 | A1 | * | 4/2009 | Okumura ........... F02D 41/1494 701/103 |
| 2010/0024790 | A1 | * | 2/2010 | Fujiwara ............. F02D 13/023 123/674 |
| 2010/0300382 | A1 | * | 12/2010 | Yahagi ................. C01B 3/323 123/3 |
| 2011/0290015 | A1 | * | 12/2011 | Ishida ................. G01N 27/419 73/335.02 |
| 2012/0037134 | A1 | | 2/2012 | Jankovic et al. |

OTHER PUBLICATIONS

Surnilla, Gopichandra et al., "Methods and Systems for Humidity Detection Via an Exhaust Gas Sensor," U.S. Appl. No. 13/973,155, filed Aug. 22, 2013, 44 pages.

Surnilla, Gopichandra et al., "Methods and Systems for Humidity and PCV Flow Detection Via an Exhaust Gas Sensor," U.S. Appl. No. 14/037,249, filed Sep. 25, 2013, 46 pages.

Anonymous, "Percent Ethanol (PM) Estimation with Sealed Fuel Tank Information (Antoine Equation & Raout's Law)," IPCOM No. 000239054, Published Oct. 6, 2014, 2 pages.

\* cited by examiner

METHODS AND SYSTEMS FOR FUEL ETHANOL CONTENT DETERMINATION VIA AN OXYGEN SENSOR

CROSS REFERENCE TO RELATED APPLICATIONS

The present application is a continuation-in-part of U.S. patent application Ser. No. 14/151,574, "METHODS AND SYSTEMS FOR FUEL ETHANOL CONTENT DETERMINATION VIA AN OXYGEN SENSOR," filed on Jan. 9, 2014, the entire contents of which are hereby incorporated by reference for all purposes.

BACKGROUND AND SUMMARY

Intake and/or exhaust gas sensors may be operated to provide indications of various exhaust gas constituents. For example, US 20120037134 describes detecting engine intake dilution using an intake gas oxygen sensor. In alternate approaches, engine dilution may be estimated by an exhaust gas oxygen sensor. The estimated engine dilution may be used to adjust various engine operating parameters, such as fueling and air-fuel ratio. As another example, U.S. Pat. No. 5,145,566 describes detecting water content in the exhaust gas using an exhaust gas oxygen sensor. In alternate approaches, water content in exhaust gas recirculated to the engine intake (EGR) may be estimated using an intake gas oxygen sensor. Water content estimated using an intake or exhaust gas oxygen sensor may be used to infer an ambient humidity during engine operation. Further still, the water content may be used to infer an alcohol content of a fuel burned in the engine.

However, the inventors have recognized that oxygen sensors (both intake and exhaust oxygen sensors) can have significant part-to-part variability. For example, without any compensation, the variability in oxygen measurement by the sensor can be in the range of 15%. This variability in the sensor output can lead to a substantial error in the measurement of fuel alcohol content and engine dilution. For example, based on the variability of the sensor, an alcohol transfer function (used to estimate fuel alcohol content based on the oxygen sensor output) may vary. If a known transfer function for a nominal sensor is used, the fuel alcohol content may be overestimated or underestimated. As such, to correctly measure the fuel alcohol content, the oxygen sensor output needs to be compensated for this part-to-part variability which is affected not only by the age of the sensor, but also ambient conditions (in particular, ambient humidity levels), as well as the presence of additional diluents (such as purge or crankcase ventilation vapors).

The above issues may be addressed and accuracy of fuel alcohol content estimation by an (intake or exhaust) oxygen sensor can be improved by a method that better compensates for sensor part-to-part variability. One example method comprises, during selected conditions, operating an oxygen sensor at a lower reference voltage where water molecules are not dissociated to generate a first output and at a higher reference voltage where water molecules are fully dissociated to generate a second output. The method further comprises learning a correction factor for the sensor based on the first and second output. The method may further comprise adjusting a parameter based on an alcohol content, the alcohol content of fuel combusted in the engine estimated based on each of the first output and the learned correction factor for the sensor. In this way, oxygen sensor reliability is improved.

In one example, during selected conditions, the oxygen sensor is operated to determine an oxygen sensor reading corrected for dry air conditions. For example, during conditions when purge and crankcase ventilation gases are not ingested in an engine intake manifold, the reference voltage of an intake oxygen sensor may be modulated. Alternatively, in embodiments where the oxygen sensor is an exhaust oxygen sensor, the selected conditions may include engine non-fueling conditions, such as a deceleration fuel shut-off (DFSO) event. Specifically, the reference voltage of the oxygen sensor may be raised from a first, lower voltage where the output (e.g., pumping current) is representative of an oxygen reading in humid conditions, to a second, higher voltage where the output (e.g., pumping current) is representative of an increase in oxygen due to the full dissociation of humid. A dry air pumping current may then be determined based on a ratio between the first output and the second output, the dry air pumping current indicative of an oxygen reading in dry air. The dry air oxygen reading (the ratio between the first and second output) is then used to determine an alcohol transfer function correction. The corrected transfer function and the humid air oxygen reading (first output) may then be used to estimate a fuel alcohol content. The estimated fuel alcohol content can then be used to estimate an engine operating parameter, such as a desired air-fuel ratio for combustion. As an example, the controller may adjust an air-fuel ratio correction based on the estimated fuel alcohol content.

In this way, the part-to-part variability of an intake or exhaust oxygen sensor may be better learned, including part-to-part variability due to sensor aging. By learning the variability, the need for a compensation resistor configured to compensate for the part-to-part variability is reduced, providing cost and component reduction benefits. By using a dry air oxygen estimate provided by the oxygen sensor to correct an alcohol transfer function, irregularities in fuel ethanol estimation may be reduced. Overall, reliability of the sensor output is increased. Further, accuracy of fuel alcohol estimated based on oxygen sensor output is also increased. Since the sensor output and fuel alcohol estimate are used to adjust various engine operating parameters, overall engine performance is improved.

It will be understood that the summary above is provided to introduce in simplified form a selection of concepts that are further described in the detailed description, which follows. It is not meant to identify key or essential features of the claimed subject matter, the scope of which is defined by the claims that follow the detailed description. Further, the claimed subject matter is not limited to implementations that solve any disadvantages noted above or in any part of this disclosure.

DETAILED DESCRIPTION

The following description relates to a method for determining an amount of alcohol in a fuel mixture (e.g., ethanol and gasoline) based on outputs from an intake air or exhaust gas sensor, such as an oxygen sensor. For example, the sensor may be operated a first, lower voltage to obtain a first output which indicates a humid air oxygen reading. The sensor may then be operated at a second, higher voltage to obtain a second output which indicates a humid air oxygen reading wherein all the humidity in the air has dissociated at the oxygen sensor. A middle voltage between the first, lower voltage and the second, higher voltage may produce an oxygen sensor output indicative of a dry air oxygen reading wherein partial dissociation of the humidity occurs. A dry air oxygen reading may then be estimated by a ratio between the first output and the second output. An alcohol transfer function may be corrected based on the estimated dry air oxygen reading and the first output may then be corrected based on the corrected alcohol transfer function to infer an amount of alcohol in fuel injected to the engine. In this manner, part-to-part variability of different oxygen sensors may be reduced such that a more accurate indication of fuel alcohol content may be determined. In one example, engine operating parameters such as spark timing and/or fuel injection amount may be adjusted based on the detected amount of alcohol in the fuel. In this manner, engine performance, fuel economy, and/or emissions may be maintained or improved despite the varying amounts of alcohol in the fuel.

Figure 1:
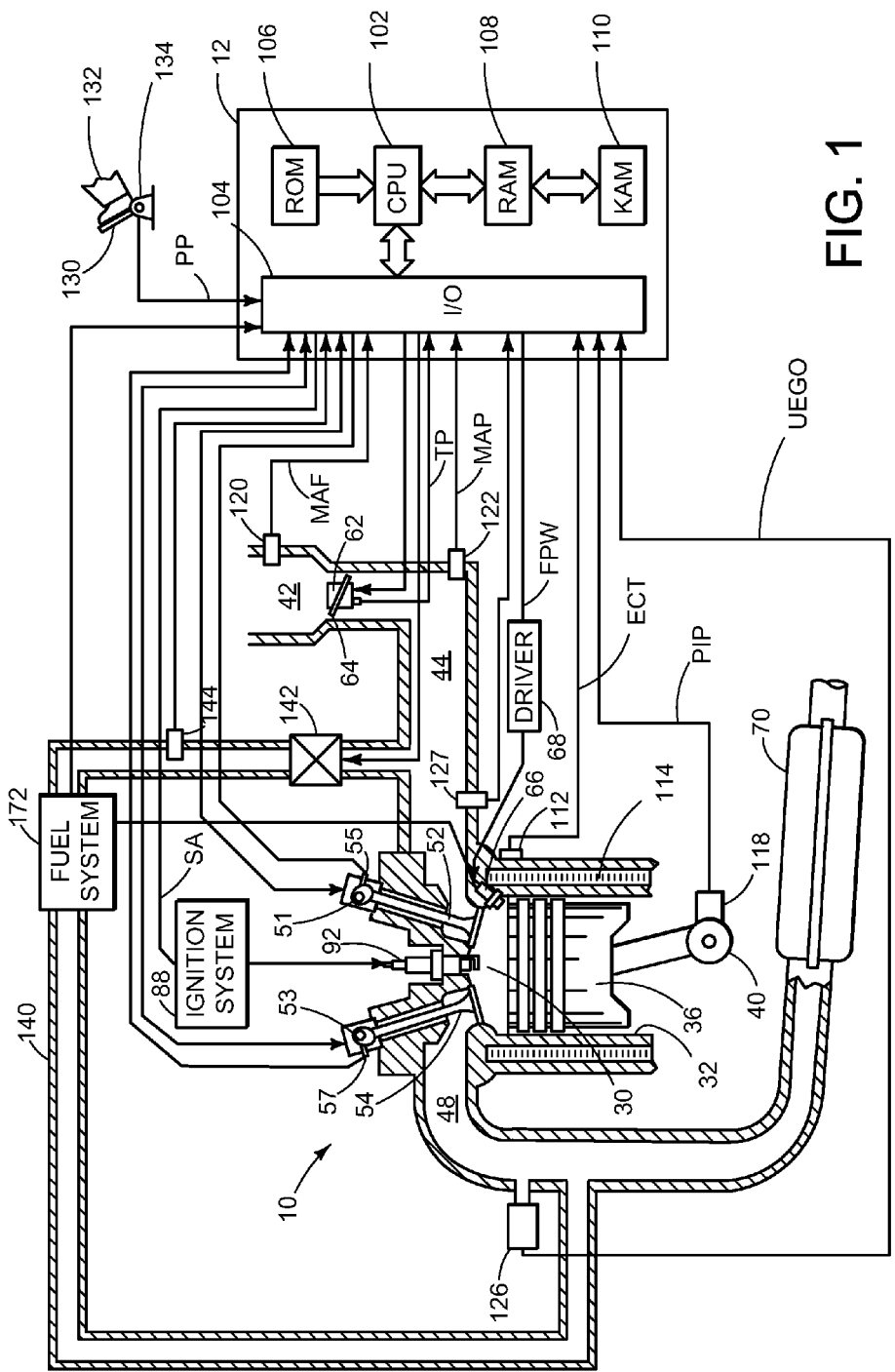
FIG. 1 shows a schematic diagram of an engine including an exhaust gas oxygen sensor and an intake gas oxygen sensor.

Referring now to FIG. 1, a schematic diagram showing one cylinder of a multi-cylinder engine 10, which may be included in a propulsion system of an automobile, is illustrated. The engine 10 may be controlled at least partially by a control system including a controller 12 and by input from a vehicle operator 132 via an input device 130. In this example, the input device 130 includes an accelerator pedal and a pedal position sensor 134 for generating a proportional pedal position signal PP. A combustion chamber (i.e., cylinder) 30 of the engine 10 may include combustion chamber walls 32 with a piston 36 positioned therein. The piston 36 may be coupled to a crankshaft 40 so that reciprocating motion of the piston is translated into rotational motion of the crankshaft. The crankshaft 40 may be coupled to at least one drive wheel of a vehicle via an intermediate transmission system. Further, a starter motor may be coupled to the crankshaft 40 via a flywheel to enable a starting operation of the engine 10.

The combustion chamber 30 may receive intake air from an intake manifold 44 via an intake passage 42 and may exhaust combustion gases via an exhaust passage 48. The intake manifold 44 and exhaust passage 48 can selectively communicate with the combustion chamber 30 via respective intake valve 52 and exhaust valve 54. In some embodiments, the combustion chamber 30 may include two or more intake valves and/or two or more exhaust valves.

In this example, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by a controller 12 to vary valve operation. The position of the intake valve 52 and exhaust valve 54 may be determined by position sensors 55 and 57, respectively. In alternative embodiments, the intake valve 52 and/or exhaust valve 54 may be controlled by electric valve actuation. For example, the cylinder 30 may alternatively include an intake valve controlled via electric valve actuation and an exhaust valve controlled via cam actuation including CPS and/or VCT systems.

In some embodiments, each cylinder of the engine 10 may be configured with one or more fuel injectors for providing fuel thereto. As a non-limiting example, the cylinder 30 is shown including one fuel injector 66. The fuel injector 66 is shown coupled directly to the cylinder 30 for injecting fuel directly therein in proportion to the pulse width of signal FPW received from the controller 12 via an electronic driver 68. In this manner, the fuel injector 66 provides what is known as direct injection (hereafter also referred to as "DI") of fuel into the combustion cylinder 30.

It will be appreciated that in an alternate embodiment, the injector 66 may be a port injector providing fuel into the intake port upstream of the cylinder 30. It will also be appreciated that the cylinder 30 may receive fuel from a plurality of injectors, such as a plurality of port injectors, a plurality of direct injectors, or a combination thereof.

A fuel tank in a fuel system 172 may hold fuels with different fuel qualities, such as different fuel compositions. These differences may include different alcohol content, different octane, different heats of vaporization, different fuel blends, and/or combinations thereof etc. The engine may use an alcohol containing fuel blend such as E85 (which is approximately 85% ethanol and 15% gasoline) or M85 (which is approximately 85% methanol and 15% gasoline). Alternatively, the engine may operate with other ratios of gasoline and ethanol stored in the tank, including 100% gasoline and 100% ethanol, and variable ratios therebetween, depending on the alcohol content of fuel supplied by the operator to the tank. Moreover, fuel characteristics of the fuel tank may vary frequently. In one example, a driver may refill the fuel tank with E85 one day, and E10 the next, and E50 the next. As such, based on the level and composition of the fuel remaining in the tank at the time of refilling, the fuel tank composition may change dynamically.

The day to day variations in tank refilling can thus result in frequently varying fuel composition of the fuel in the fuel system 172, thereby affecting the fuel composition and/or fuel quality delivered by the injector 66. The different fuel compositions injected by the injector 66 may herein be referred to as a fuel type. In one example, the different fuel compositions may be qualitatively described by their research octane number (RON) rating, alcohol percentage, ethanol percentage, etc.

It will be appreciated that while in one embodiment, the engine may be operated by injecting the variable fuel blend via a direct injector, in alternate embodiments, the engine may be operated by using two injectors and varying a relative amount of injection from each injector. It will be further appreciated that when operating the engine with a boost from a boosting device such as a turbocharger or supercharger (not shown), the boosting limit may be increased as an alcohol content of the variable fuel blend is increased.

Continuing with FIG. 1, the intake passage 42 may include a throttle 62 having a throttle plate 64. In this particular example, the position of the throttle plate 64 may be varied by the controller 12 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle plate 64 may be provided to the controller 12 by a throttle position signal TP. The intake passage 42 may include a mass air flow sensor 120 and a manifold air pressure sensor 122 for providing respective signals MAF and MAP to controller 12.

An ignition system 88 can provide an ignition spark to the combustion chamber 30 via a spark plug 92 in response to a spark advance signal SA from the controller 12, under select operating modes. Though spark ignition components are shown, in some embodiments, the combustion chamber 30 or one or more other combustion chambers of the engine 10 may be operated in a compression ignition mode, with or without an ignition spark.

An exhaust gas sensor 126 is shown coupled to the exhaust passage 48 upstream of an emission control device 70. The sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor. The emission control device 70 is shown arranged along the exhaust passage 48 downstream of the exhaust gas sensor 126. The device 70 may be a three way catalyst (TWC), $NO_x$ trap, various other emission control devices, or combinations thereof. In some embodiments, during operation of engine 10, emission control device 70 may be periodically reset by operating at least one cylinder of the engine within a particular air/fuel ratio.

As shown in the example of FIG. 1, the system further includes an intake air sensor 127 coupled to the intake passage 44. The sensor 127 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor.

Further, in the disclosed embodiments, an exhaust gas recirculation (EGR) system may route a desired portion of exhaust gas from the exhaust passage 48 to the intake passage 44 via an EGR passage 140. The amount of EGR provided to the intake passage 44 may be varied by the controller 12 via an EGR valve 142. Further, an EGR sensor 144 may be arranged within the EGR passage 140 and may provide an indication of one or more of pressure, temperature, and concentration of the exhaust gas. Under some conditions, the EGR system may be used to regulate the temperature of the air and fuel mixture within the combustion chamber, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

The controller 12 is shown in FIG. 1 as a microcomputer, including a microprocessor unit 102, input/output ports 104, an electronic storage medium for executable programs and calibration values shown as read only memory chip 106 in this particular example, random access memory 108, keep alive memory 110, and a data bus. The controller 12 may receive various signals from sensors coupled to the engine 10, in addition to those signals previously discussed, including measurement of inducted mass air flow (MAF) from the mass air flow sensor 120; engine coolant temperature (ECT) from a temperature sensor 112 coupled to a cooling sleeve 114; a profile ignition pickup signal (PIP) from a Hall effect sensor 118 (or other type) coupled to the crankshaft 40; throttle position (TP) from a throttle position sensor; and absolute manifold pressure signal, MAP, from the sensor 122. Engine speed signal, RPM, may be generated by the controller 12 from signal PIP.

The storage medium read-only memory 106 can be programmed with computer readable data representing instructions executable by the processor 102 for performing the methods described below as well as other variants that are anticipated but not specifically listed.

As described above, FIG. 1 shows only one cylinder of a multi-cylinder engine, and each cylinder may similarly include its own set of intake/exhaust valves, fuel injector, spark plug, etc.

Figure 2:
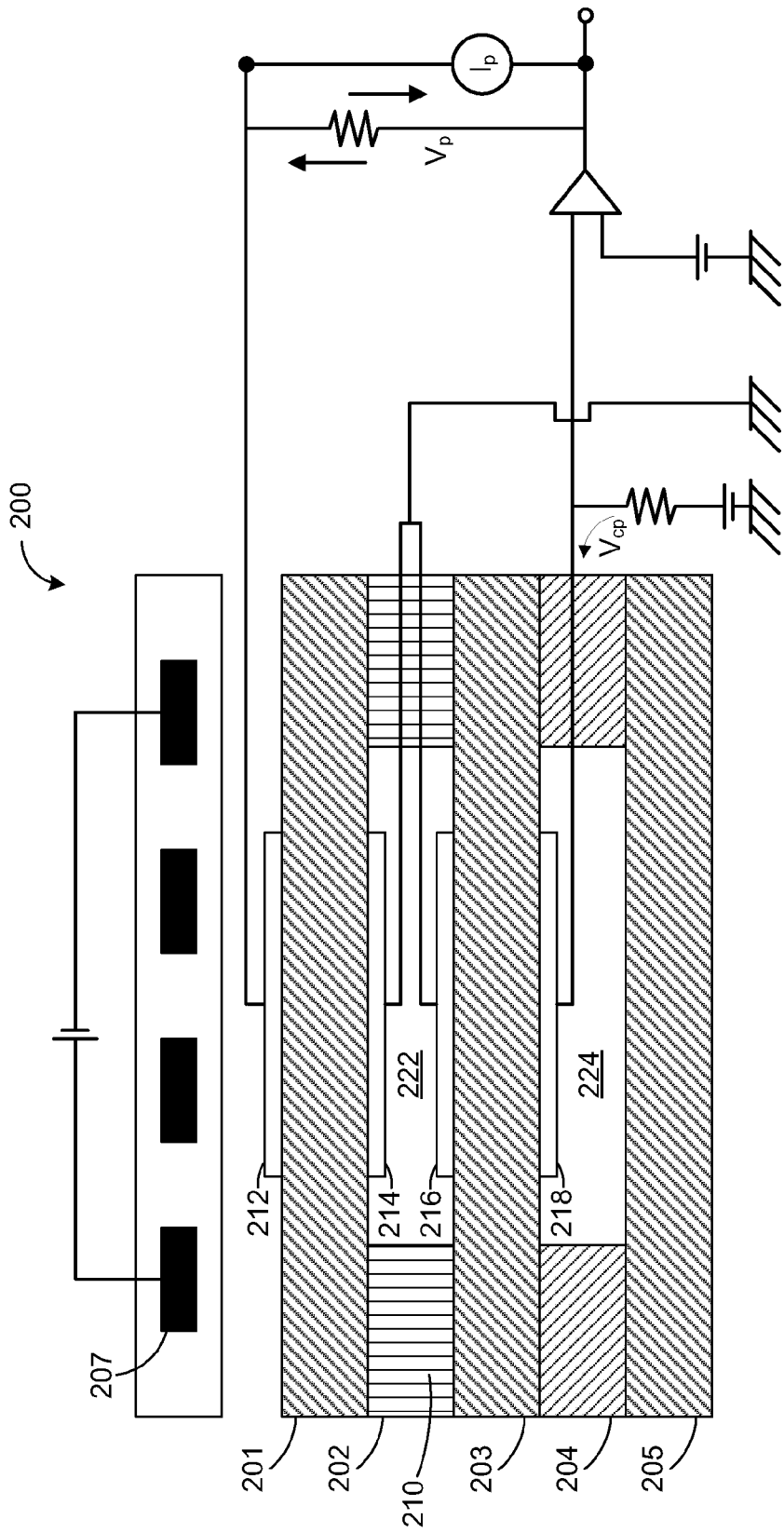
FIG. 2 shows a schematic diagram of an example oxygen sensor.

Next, FIG. 2 shows a schematic view of an example embodiment of an oxygen sensor 200 configured to measure a concentration of oxygen ($O_2$) in an intake airflow in an intake passage or an exhaust gas stream in an exhaust passage. The sensor 200 may operate as UEGO sensor 126 of FIG. 1, for example. The sensor 200 comprises a plurality of layers of one or more ceramic materials arranged in a stacked configuration. In the embodiment of FIG. 2, five ceramic layers are depicted as layers 201, 202, 203, 204, and 205. These layers include one or more layers of a solid electrolyte capable of conducting ionic oxygen. Examples of suitable solid electrolytes include, but are not limited to, zirconium oxide-based materials. Further, in some embodiments, a heater 207 may be disposed in thermal communication with the layers to increase the ionic conductivity of the layers. While the depicted oxygen sensor is formed from five ceramic layers, it will be appreciated that the oxygen sensor may include other suitable numbers of ceramic layers.

The layer 202 includes a material or materials creating a diffusion path 210. The diffusion path 210 is configured to introduce exhaust gases into a first internal cavity 222 via diffusion. The diffusion path 210 may be configured to allow one or more components of intake air or exhaust gases, including but not limited to a desired analyte (e.g., $O_2$), to diffuse into internal cavity 222 at a more limiting rate than the analyte can be pumped in or out by a pumping electrodes pair 212 and 214. In this manner, a stoichiometric level of $O_2$ may be obtained in the first internal cavity 222.

The sensor 200 further includes a second internal cavity 224 within the layer 204 separated from the first internal cavity 222 by the layer 203. The second internal cavity 224 is configured to maintain a constant oxygen partial pressure equivalent to a stoichiometric condition, e.g., an oxygen level present in the second internal cavity 224 is equal to that which the intake air or exhaust gas would have if the air-fuel ratio was stoichiometric. The oxygen concentration in the second internal cavity 224 is held constant by pumping voltage $V_{cp}$. Herein, the second internal cavity 224 may be referred to as a reference cell.

A pair of sensing electrodes 216 and 218 is disposed in communication with the first internal cavity 222 and the reference cell 224. The sensing electrodes pair 216 and 218 detects a concentration gradient that may develop between the first internal cavity 222 and the reference cell 224 due to an oxygen concentration in the intake air or exhaust gas that is higher than or lower than the stoichiometric level. A high oxygen concentration may be caused by a lean intake air or exhaust gas mixture, while a low oxygen concentration may be caused by a rich mixture.

A pair of pumping electrodes 212 and 214 is disposed in communication with the internal cavity 222, and is configured to electrochemically pump a selected gas constituent (e.g., $O_2$) from internal cavity 222 through layer 201 and out of the sensor 200. Alternatively, the pair of pumping electrodes 212 and 214 may be configured to electrochemically pump a selected gas through layer 201 and into internal cavity 222. Herein, the pumping electrodes pair 212 and 214 may be referred to as an $O_2$ pumping cell.

The electrodes 212, 214, 216, and 218 may be made of various suitable materials. In some embodiments, the electrodes 212, 214, 216, and 218 may be at least partially made of a material that catalyzes the dissociation of molecular oxygen. Examples of such materials include, but are not limited to, electrodes containing platinum and/or silver.

The process of electrochemically pumping the oxygen out of or into the internal cavity 222 includes applying a voltage $V_p$ across the pumping electrode pair 212 and 214. The pumping voltage $V_p$ applied to the $O_2$ pumping cell pumps oxygen into or out of the first internal cavity 222 in order to maintain a stoichiometric level of oxygen in the cavity pumping cell. The resulting pumping current $I_p$ is proportional to the concentration of oxygen in the exhaust gas. A control system (not shown in FIG. 2) generates the pumping current signal $I_p$ as a function of the intensity of the applied pumping voltage $V_p$ required to maintain a stoichiometric level within the first internal cavity 222. Thus, a lean mixture will cause oxygen to be pumped out of the internal cavity 222 and a rich mixture will cause oxygen to be pumped into the internal cavity 222.

It should be appreciated that the oxygen sensor described herein is merely an example embodiment of an oxygen sensor, and that other embodiments of oxygen sensors may have additional and/or alternative features and/or designs.

As elaborated below, the oxygen sensor of FIG. 2 can be advantageously used to estimate an accurate amount of alcohol in the fuel burned in the engine despite part-to-part variability of the intake or exhaust oxygen sensor. In particular, by determining an estimated dry air oxygen reading based on a ratio between an oxygen sensor output at a first, lower voltage and an oxygen sensor output at a second, higher voltage, an alcohol transfer function correction may be determined. The corrected transfer function may then be applied to a humid air oxygen reading determined at the first, lower voltage to estimate a fuel alcohol content.

Figure 3:
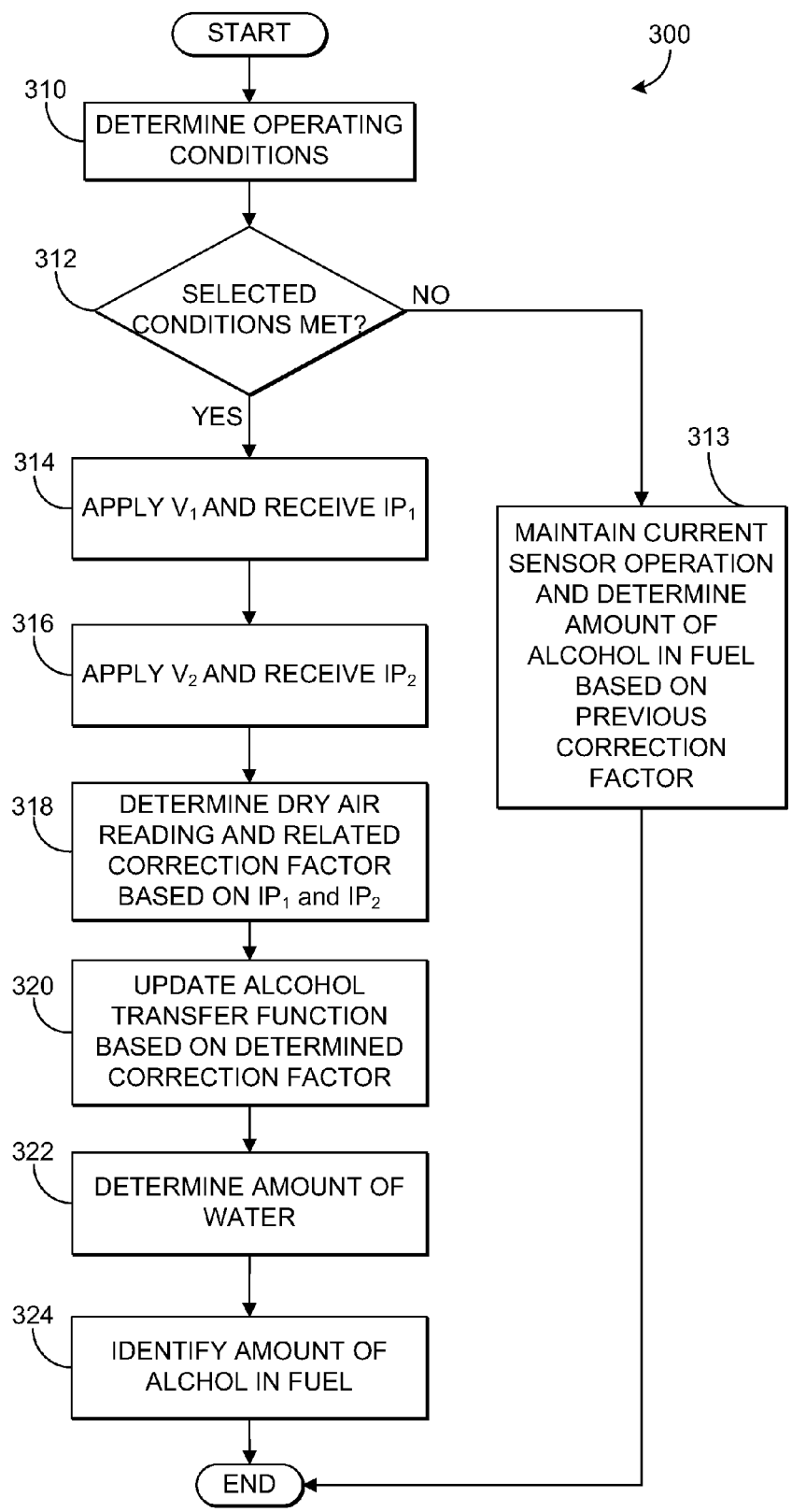
FIG. 3 shows a flow chart illustrating a routine for accurately estimating an amount of alcohol in fuel, while correcting an alcohol transfer function for effects of oxygen sensor part-to-part variation.

Continuing to FIG. 3, a flow chart illustrating a routine 300 for accurately estimating an amount of alcohol in fuel, while correcting an alcohol transfer function for effects of part-to-part variation of an oxygen sensor, such as the oxygen sensor 200 described above with reference to FIG. 2, is shown. Specifically, the routine 300 determines an amount of alcohol in the fuel injected to the engine, and thus the fuel type, based on voltages applied to a pumping cell of the sensor during selected engine fueling conditions and further based on an alcohol transfer function correction.

At 310 of routine 300, engine operating conditions are determined. Engine operating conditions may include but are not limited to air-fuel ratio, amount of EGR entering the combustion chambers, and fueling conditions, for example.

Once the engine operating conditions are determined, routine 300 continues to 312 where it is determined if selected conditions are met. For example, when the oxygen is an intake oxygen sensor positioned in the intake passage, the selected conditions may include EGR being enabled and no purge or crankcase ventilation gases being received in the intake manifold. As another example, when the oxygen sensor is an exhaust gas oxygen sensor positioned in the exhaust passage, the selected conditions may include engine non-fueling conditions. Non-fueling conditions include vehicle deceleration conditions and engine operating conditions in which the fuel supply is interrupted but the engine continues spinning and at least one intake valve and one exhaust valve are operating; thus, air is flowing through one or more of the cylinders, but fuel is not injected in the cylinders. Under non-fueling conditions, combustion is not carried out and ambient air may move through the cylinder from the intake to the exhaust. In this way, a sensor, such as an intake or exhaust oxygen sensor, may receive ambient air on which measurements, such as ambient humidity detection, may be performed.

As noted, non-fueling conditions may include, for example, deceleration fuel shut-off (DFSO). DFSO is responsive to the operator pedal (e.g., in response to a driver tip-out and where the vehicle accelerates greater than a threshold amount). DSFO conditions may occur repeatedly during a drive cycle, and, thus, numerous indications of the ambient humidity may be generated throughout the drive cycle, such as during each DFSO event. As such, the fuel type may be identified accurately based on an amount of water in the exhaust gas despite fluctuations in humidity between drive cycles or even during the same drive cycle.

Continuing with FIG. 3, if it is determined that the selected operating conditions are not met, the routine 300 continues to 313 to continue current oxygen sensor operation (at the current pumping voltage) and determine the amount of alcohol in the fuel based on a previously determined correction factor. Conversely, if is determined that selected operating conditions are met, routine 300 continues to 314 where a first pumping voltage ($V_1$) is applied to the oxygen pumping cell of the exhaust gas sensor and a first pumping current ($I_{p1}$) is received. The first pumping voltage may have a value such that oxygen is pumped from the cell, but low enough that oxygen compounds such as $H_2O$ (e.g., water) are not dissociated (e.g., $V_1$=450 mV). For example, at the first pumping voltage, the oxygen sensor may not dissociate any water molecules. Application of the first voltage generates an output of the sensor in the form of the first pumping current ($I_{p1}$) that is indicative of the amount of oxygen in the sample gas. In this example, because the engine is under selected conditions (such as non-fueling conditions), the amount of oxygen may correspond to the amount of oxygen in the fresh air surrounding the vehicle, or a humid air oxygen reading.

Once the amount of oxygen is determined, routine 300 proceeds to 316 where a second pumping voltage ($V_2$) is applied to the oxygen pumping cell of the sensor and a second pumping ($I_{p2}$) current is received. The second voltage may be greater than the first voltage applied to the sensor. In particular, the second voltage may have a value high enough to dissociate a desired oxygen compound. For example, the second voltage may be high enough to dissociate all $H_2O$ molecules into hydrogen and oxygen (e.g., $V_2$=1.1 V). Application of the second voltage generates the second pumping current ($I_2$) that is indicative of the amount of oxygen and water in the sample gas. It will be understood that the term "water" in the "amount of oxygen and water" as used herein refers to the amount of oxygen from the dissociated $H_2O$ molecules in the sample gas.

Figure 4:
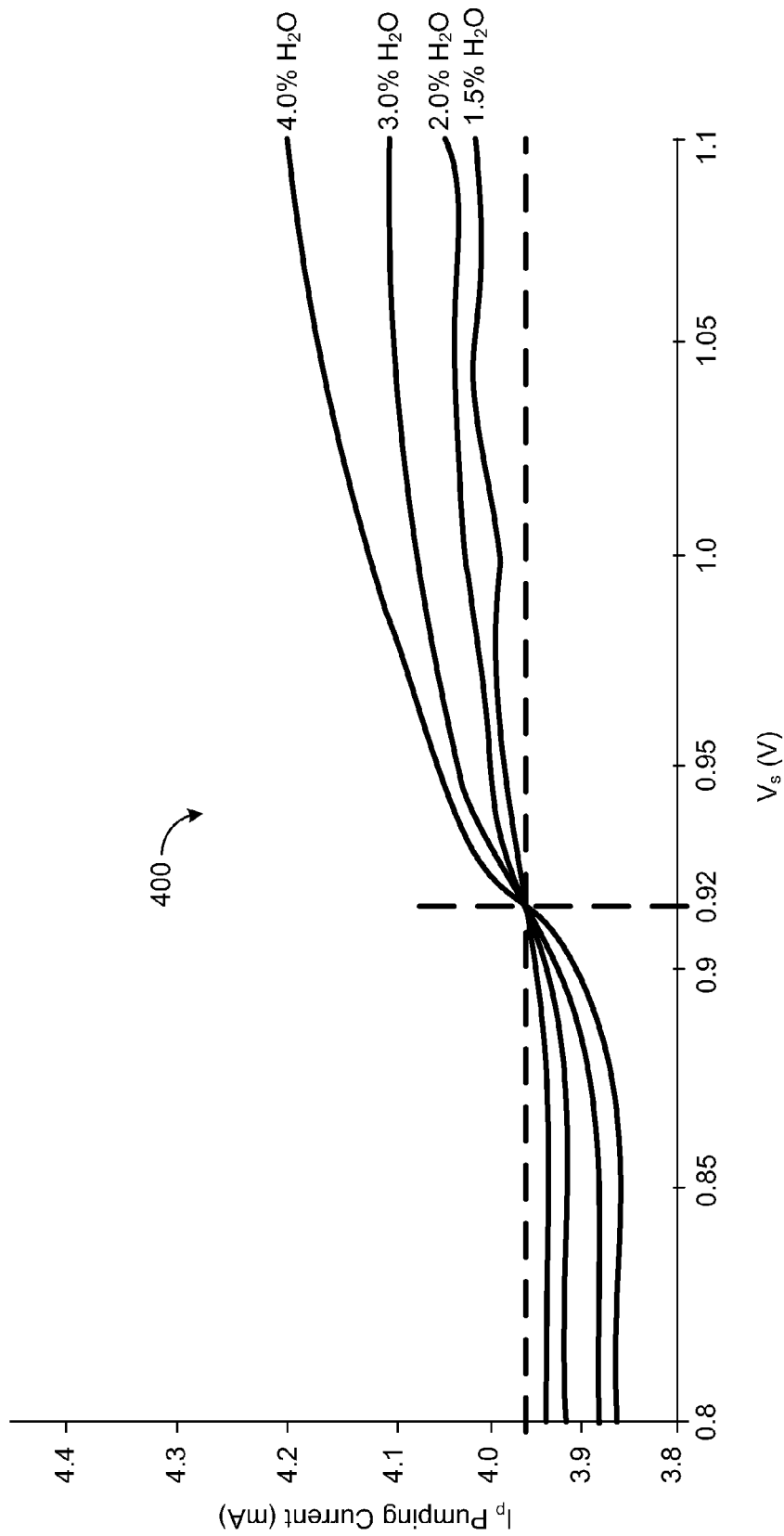
FIG. 4 shows a graph depicting oxygen sensor output under various humidity conditions with respect to applied voltage.

In one particular example, the second voltage may be 1080 mV, at which the water in the air is fully (e.g., completely) dissociated (e.g., 100% of the water in the air is dissociated at 1080 mV). This second voltage may be larger than a third, middle voltage where water in the air is partially dissociated (e.g., approximately 40% of the water in the air is dissociated). In one example, the third, middle voltage may be about 920 mV. In another example, the third, middle voltage may be about 950 mV. As an example, a graph 400 of FIG. 4 shows oxygen sensor output over a range of humidity conditions (e.g., from 1.5% humidity to 4% humidity). As shown, the sensor output at 920 mV corresponds to a dry air reading under the range of humidity conditions. The sensor output at 1.1 V corresponds to a humid air reading where all the water in the air has been dissociated at the sensor and the sensor output at 4.5 V corresponds to a humid air reading where no water in the air has been dissociated. Thus, a dry air oxygen reading may be obtained by a ratio of oxygen sensor outputs when the oxygen sensor is operated at 4.5 V and 1.1V. In an alternate embodiment, the dry air oxygen reading may be obtained by a ratio of oxygen sensor output when the oxygen sensor is operated at a voltage below 0.92 V where water is not dissociated (e.g., not even partially dissociated) and a voltage above 0.92 V where water is fully dissociated (e.g., 100% dissociated).

At 318, the dry air oxygen reading and related correction factor are determined based on the first pumping current and the second pumping current. For example, as described above, by operating the sensor at 450 mV (or a similar voltage where no water is dissociated at the sensor), a lower pumping current and oxygen reading may be obtained and by operating the sensor at 1080 mV (or a similar voltage where all water is dissociated at the sensor) a higher pumping current and oxygen reading may be obtained. A dry air pumping current indicative of a dry air oxygen reading may then be estimated from a ratio between the lower pumping current and the higher pumping current. For example, a sum of 40% of the higher pumping current and 60% of the lower pumping current may be substantially equal to the dry air pumping current and oxygen reading. In an alternate example, different percentages of the higher and lower pumping current may be added together to determine the dry air pumping current. For example, if the higher or lower voltage differ from 450 mV and 1080 mV, respectively, the corresponding percentages used to determine the ratio between the higher and lower pumping currents may differ proportionally.

The estimated dry air oxygen reading based on the ratio between the higher and lower pumping currents (e.g., higher and lower oxygen sensor outputs corresponding to the higher and lower voltages) may then be used to determine the correction factor, or alcohol transfer function correction. As described above, the correction factor is a factor that compensates for part-to-part variability of the sensor. In one example, the correction factor may be determined based on a ratio of a reference sensor output relative to the estimated dry air oxygen reading at the ratio between the first and second voltage. Said another way, the correction factor may be determined based on a ratio of the reference sensor output relative to a ratio of the first and second outputs of the sensor generated by applying the first and second voltages, respectively. Once the correction factor is determined, the alcohol transfer function is updated based on the determined correction factor at 320.

Once the first and second pumping currents are generated, an amount of water in the sample gas may be determined at 322 of routine 300 in FIG. 3. For example, when the second pumping current is high enough to dissociate substantially all water molecules in the sample gas, the first pumping current may be subtracted from the second pumping current to determine a value that corresponds to an amount of water.

Finally, the amount of alcohol in the fuel, and thus the fuel type, may be identified at 324. For example, the corrected transfer function may be applied to the first pumping current such that an accurate indication of an amount of alcohol (e.g., a percent of ethanol) in the fuel injected to the engine is determined. In some embodiments, the computer readable storage medium of the control system receiving communication from the sensor may include instructions for identifying the amount of alcohol.

Thus, based on sensor outputs (e.g., pumping currents) generated responsive to voltages applied to the oxygen pumping cell of the intake air or exhaust gas sensor during engine fueling and non-fueling conditions and the transfer function correction factor, an accurate indication of the amount alcohol (e.g., percent ethanol) in the fuel may be identified. Further, once the fuel type is determined, various engine operating parameters may be adjusted to maintain engine and/or emissions efficiency, as will be described in detail below.

Method 300 may further include, after 318, determining a correction oxygen sensor output based on the correction factor and the measured oxygen (e.g., the first output). The corrected oxygen sensor output may be the oxygen sensor measurement corrected for the part-to-party variability and/or change in the oxygen sensor reading over time. The corrected oxygen sensor reading may then be used for additional engine controls and estimates such as an estimate of EGR flow if the oxygen sensor is an intake oxygen sensor positioned in the engine intake.

Figure 5:
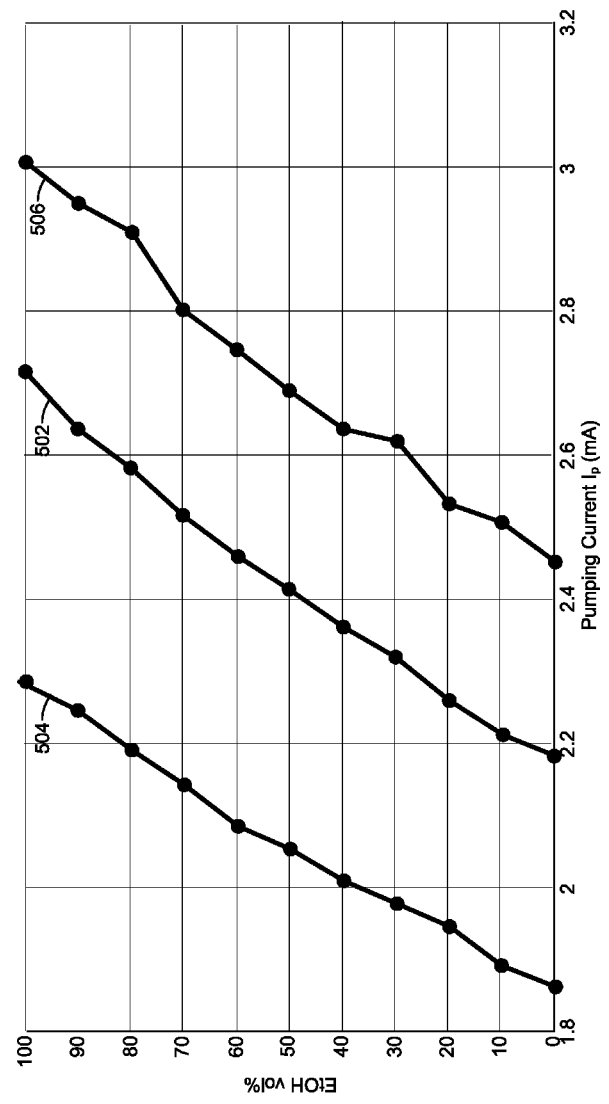
FIG. 5 shows a graph depicting impact of oxygen sensor part-to-part variability on fuel ethanol estimation.

FIG. 5 shows a graph illustrating the difference in percent ethanol due to sensor-to-sensor variation. For example, a curve 502 shows a first transfer function for a normal sensor. A curve 504 shows a second transfer function for a sensor which indicates a lower than normal percent ethanol. A curve 506 shows a third transfer function for a sensor which indicates a higher than normal percent ethanol. As shown, due to differences such as part-to-part variability, different sensors may indicate different values for percent ethanol in the same environment. As such, the alcohol transfer function may be corrected as described above based on first and second outputs of the oxygen sensor such that sensor-to-sensor variation is reduced and a more accurate indication of the amount of alcohol in the fuel may be identified.

Figure 6:
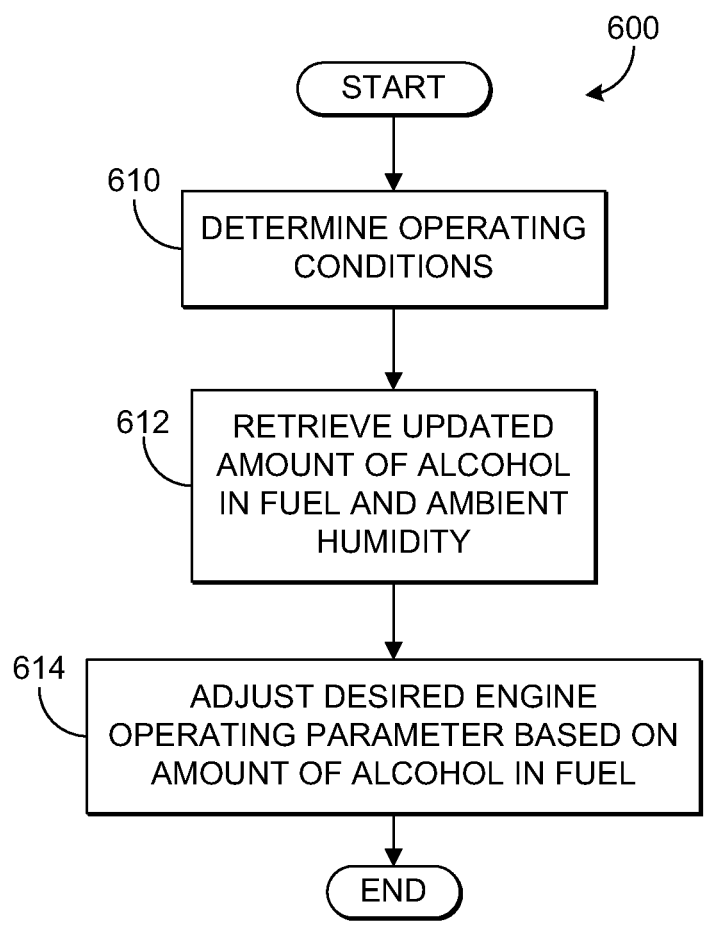
FIG. 6 shows a flow chart illustrating a routine for controlling an engine based on the output of an intake or exhaust gas oxygen sensor.

Referring now to FIG. 6, a flow chart depicting a general control routine 600 for adjusting engine operating parameters based on an amount of alcohol (e.g., a corrected amount of alcohol determined based on the corrected transfer function as described above) in fuel injected to the engine is shown. Specifically, one or more engine operating parameters may be adjusted corresponding to a change in the amount of alcohol in the fuel. For example, fuels containing different amounts of alcohol may have different properties such as viscosity, octane number, latent enthalpy of vaporization, etc. As such, engine performance, fuel economy, and/or emissions may be degraded if one or more appropriate operating parameters are not adjusted.

At 610 of routine 600, engine operating conditions are determined. Engine operating conditions may include, for example, air-fuel ratio, fuel injection timing, and spark timing. For example, the ratio of air to fuel which is stoichiometric may vary for varying types (e.g., 14.7 for gasoline, 9.76 for E85) and fuel injection timing and spark timing may need to be adjusted based on the fuel type.

Once the operating conditions are determined, an updated amount of alcohol in the fuel mixture and the ambient humidity are determined at 612 of routine 600. As described above, the fuel type may be determined based on outputs from an exhaust gas or intake air sensor. After the fuel type is known, routine 600 proceeds to 614 where, under selected operating conditions such as cold start or transient fueling conditions, one or more desired operating parameters are adjusted based on the amount of alcohol in the fuel. For example, the system may adjust a desired air-fuel ratio for combustion (e.g., the stoichiometric air-fuel ratio) based on the estimated amount of alcohol in the fuel. Further, feedback air-fuel ratio control gains may be adjusted based on the amount of alcohol in the fuel. Further still, the desired air-fuel ratio during cold starting may be adjusted based on the amount of alcohol in the fuel. Further still, spark angle (such as spark retard) and/or boost levels may be adjusted based on the amount of alcohol in the fuel.

In some embodiments, for example, the timing and/or amount of the fuel injection in one or more cylinders may be adjusted. For example, if it is determined that the amount of alcohol in the fuel is increased (e.g., from 10% ethanol to 30% ethanol) during cold start conditions, the amount of fuel injected to the engine may be increased.

As another example, spark timing may be adjusted based on the detected amount of alcohol in the fuel. For example, if the detected percentage of alcohol is lower than previously detected (e.g., from 85% ethanol to 50% ethanol), the spark timing may be retarded in order to achieve a higher engine output or boost without knock.

Thus, various engine operating parameters may be adjusted during selected operating conditions based on a detected amount of alcohol in the fuel injected to the cylinders of the engine. In this manner, engine and/or emissions efficiency as well as fuel economy may be maintained or improved.

As one embodiment, a method comprises during engine non-fueling conditions, applying each of a first, lower voltage where water molecules are not dissociated and a second, higher voltage where water molecules are fully dissociated to an exhaust oxygen sensor. The method further comprises learning a correction factor for the sensor based on a ratio of first and second outputs generated upon applying the first and second voltages, respectively and estimating an ethanol content of fuel combusted in the engine by applying the learned correction factor to a transfer function based on the first output. The engine non-fueling conditions include a deceleration fuel shut-off event, the method further comprising, adjusting an engine operating parameter based on the estimated fuel ethanol content, the parameter including an air-fuel ratio for combustion. The first output includes a first pumping current generated responsive to applying the first, lower voltage and the second output includes a second pumping current generated responsive to applying the second, higher voltage, the first and second outputs indicative of a humid air oxygen amount, and wherein the first, lower voltage is below a middle voltage and the second, higher voltage is above the middle voltage, the middle voltage being a voltage where water molecules in the air are partially dissociated, the middle voltage generating a third pumping current indicative of a dry air oxygen amount. In one example, the middle voltage may be 920 mV while the first, lower voltage is 450 mV and the second, higher voltage is 1080 mV. Additionally, the exhaust gas oxygen sensor is located upstream of an exhaust catalyst and upstream of an inlet of an EGR passage configured to recirculate exhaust residuals from an exhaust manifold to an intake manifold of the engine.

As another embodiment, a method comprises while purge and crankcase ventilation gases are not ingested in an engine, applying each of a first, lower voltage where water molecules are not dissociated and a second, higher voltage where water molecules are fully dissociated to an intake oxygen sensor. The method further comprises learning a correction factor for the sensor based on a ratio of first and second outputs generated upon applying the first and second voltages, respectively and estimating an ethanol content of fuel combusted in the engine by applying the learned correction factor to a transfer function based on the first output. The first output includes a first pumping current generated responsive to applying the first, lower voltage, the first output indicative of a humid air oxygen amount, and the second output includes a second pumping current generated responsive to applying the second, higher voltage, the second output indicative of an increase in oxygen due to dissociation of humidity, and a ratio between the first output and second output is indicative of a dry air oxygen amount. The intake oxygen sensor is located upstream of an intake throttle, and downstream of an outlet of an EGR passage configured to recirculate exhaust residuals from an exhaust manifold to an intake manifold of the engine. The method further comprising estimating an EGR flow rate in the EGR passage based on an adjusted output of the intake oxygen sensor, the adjusted output of the intake oxygen sensor based on an output of the intake oxygen sensor and the learned correction factor.

Note that the example control and estimation routines included herein can be used with various engine and/or vehicle system configurations. The control methods and routines disclosed herein may be stored as executable instructions in non-transitory memory. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for an engine, comprising:
during selected conditions,
operating an oxygen sensor at a lower reference voltage where water molecules in a sample gas are not dissociated to generate a first output and at a higher reference voltage where all water molecules in the sample gas are fully dissociated to generate a second output; and
learning a correction factor for the sensor based on the first and second outputs.

2. The method of claim 1, further comprising adjusting a parameter based on an alcohol content, the alcohol content of fuel combusted in the engine estimated based on each of the first output and the learned correction factor.

3. The method of claim 2, wherein the parameter is a desired engine air-fuel ratio for combustion, and wherein the correction factor is based on a dry air pumping current, the dry air pumping current based on a weighted sum of the first and second outputs.

4. The method of claim 1, wherein the first output includes a first pumping current generated responsive to the operating at the lower reference voltage and wherein the second output includes a second pumping current generated responsive to operating at the higher reference voltage.

5. The method of claim 1, wherein the first output is indicative of a humid air oxygen reading and the second output is indicative of an increase in oxygen due to dissociation of humid air and wherein a dry air pumping current is based on a ratio between the first output and the second output, the dry air pumping current indicative of a dry air oxygen reading.

6. The method of claim 1, wherein the correction factor is a dry air correction factor that compensates for part-to-part variability of the sensor, and wherein learning the correction factor based on the first and second outputs includes learning the correction factor based on a ratio of a reference sensor output relative to a ratio between the first output and the second output.

7. The method of claim 6, wherein a reference alcohol transfer function of the sensor is based on the reference sensor output.

8. The method of claim 7, wherein the alcohol content of fuel estimated based on each of the first output and the learned correction factor includes:
adjusting the reference alcohol transfer function of the sensor based on the learned correction factor; and
applying the adjusted alcohol transfer function to the first output of the sensor.

9. The method of claim 1, wherein the oxygen sensor is a universal exhaust gas oxygen sensor coupled to an exhaust manifold of the engine, upstream of an exhaust catalyst, and where the higher reference voltage is 1080 mV.

10. The method of claim 9, wherein the selected conditions include engine non-fueling conditions, the engine non-fueling conditions including a deceleration fuel shut-off event.

11. The method of claim 1, wherein the oxygen sensor is an intake oxygen sensor coupled to an intake manifold of the engine, upstream of an intake compressor.

12. The method of claim 11, wherein the selected conditions include EGR being enabled and no purge or crankcase ventilation gases being received in the intake manifold.

13. A method, comprising:
during engine non-fueling conditions,
applying each of a first, lower voltage where water molecules are not dissociated and a second, higher voltage where all water molecules are fully dissociated to an exhaust oxygen sensor;
learning a correction factor for the sensor based on a dry air pumping current, the dry air pumping current based on a ratio of first and second outputs generated upon applying the first and second voltages, respectively; and
estimating an ethanol content of fuel combusted in the engine by applying the learned correction factor to a transfer function based on the first output.

14. The method of claim 13, wherein the engine non-fueling conditions include a deceleration fuel shut-off event, the method further comprising, adjusting an engine operating parameter based on the estimated fuel ethanol content, the parameter including an air-fuel ratio for combustion, and wherein the second voltage is 1100 mV.

15. The method of claim 13, wherein the first output includes a first pumping current generated responsive to applying the first, lower voltage and the second output includes a second pumping current generated responsive to applying the second, higher voltage, the first and second outputs indicative of a humid air oxygen amount, and wherein the first, lower voltage is below a middle voltage and the second, higher voltage is above the middle voltage, the middle voltage generating a third pumping current indicative of a dry air oxygen amount.

16. The method of claim 13, wherein the exhaust gas oxygen sensor is located upstream of an exhaust catalyst and upstream of an inlet of an EGR passage configured to recirculate exhaust residuals from an exhaust manifold to an intake manifold of the engine.

17. A method, comprising:
while purge and crankcase ventilation gases are not ingested in an engine,
applying each of a first, lower voltage where water molecules are not dissociated and a second, higher voltage where water molecules are fully dissociated to an intake oxygen sensor;
learning a correction factor for the sensor based on a ratio of first and second outputs generated upon applying the first and second voltages, respectively; and
estimating an ethanol content of fuel combusted in the engine by applying the learned correction factor to a transfer function based on the first output.

18. The method of claim 17, wherein the first output includes a first pumping current generated responsive to applying the first, lower voltage, the first output indicative of a humid air oxygen amount, and wherein the second output includes a second pumping current generated responsive to applying the second, higher voltage, the second output indicative of an increase in oxygen due to dissociation of humidity, and wherein a ratio between the first output and second output is indicative of a dry air oxygen amount.

19. The method of claim 17, wherein the intake oxygen sensor is located upstream of an intake throttle, and downstream of an outlet of an EGR passage configured to recirculate exhaust residuals from an exhaust manifold to an intake manifold of the engine.

20. The method of claim 19, further comprising estimating an EGR flow rate in the EGR passage based on an adjusted output of the intake oxygen sensor, the adjusted output of the intake oxygen sensor based on an output of the intake oxygen sensor and the learned correction factor.

* * * * *